US012642976B2

(12) United States Patent
Landherr et al.

(10) Patent No.: US 12,642,976 B2
(45) Date of Patent: Jun. 2, 2026

(54) SYSTEMS AND METHODS FOR ESTABLISHING SECURE COMMUNICATIONS BETWEEN MEDICAL DEVICE SYSTEM COMPONENTS

(71) Applicant: Cardiac Pacemakers, Inc., St. Paul, MN (US)

(72) Inventors: Daniel Joseph Landherr, Wyoming, MN (US); Ron A. Balczewski, Bloomington, MN (US); Keith R. Maile, New Brighton, MN (US); William J. Linder, Golden Valley, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 331 days.

(21) Appl. No.: 18/200,987

(22) Filed: May 23, 2023

(65) Prior Publication Data

US 2023/0381525 A1     Nov. 30, 2023

Related U.S. Application Data

(60) Provisional application No. 63/346,460, filed on May 27, 2022.

(51) Int. Cl.
A61N 1/372          (2006.01)
A61N 1/378          (2006.01)

(52) U.S. Cl.
CPC ..... A61N 1/37229 (2013.01); A61N 1/37252 (2013.01); A61N 1/3787 (2013.01)

(58) Field of Classification Search
CPC .............. A61N 1/37252; A61N 1/3787; A61N 1/37223; A61N 1/37254
See application file for complete search history.

(56) References Cited

U.S. PATENT DOCUMENTS 7,615,012 B2    11/2009    Von Arx et al.
7,743,151 B2    6/2010    Vallapureddy et al.
(Continued)

FOREIGN PATENT DOCUMENTS

WO          03095024          11/2003
WO    WO-2005091205 A2 *    9/2005    ......... A61N 1/37254

*Primary Examiner* — Brian T Gedeon
(74) *Attorney, Agent, or Firm* — Pauly, DeVries Smith & Deffner LLC

(57)          ABSTRACT

Embodiments herein relate to medical device systems including features to enable secure wireless communications between components thereof. In an embodiment, a medical device system is included having an implantable medical device packaging unit and an implantable device. The implantable device can include a control circuit and a communications antenna. The implantable device can be configured to fit within the implantable medical device packaging unit prior to implantation in a patient. The system can also include a data bearing tag, wherein the data bearing tag is disposed on or in the implantable medical device packaging unit. In some embodiments the system can also include an external communication device. The external communication device can be configured to receive data from the data bearing tag enabling secure wireless communications between the implantable device and the external communication device. Other embodiments are also included herein.

20 Claims, 13 Drawing Sheets

(56)             References Cited

U.S. PATENT DOCUMENTS

| | | | |
|---|---|---|---|
| 7,818,067 B2 | 10/2010 | Healy et al. | |
| 7,831,828 B2 | 11/2010 | Von Arx et al. | |
| 7,844,341 B2 | 11/2010 | Von Arx et al. | |
| 8,374,693 B2 | 2/2013 | Chavan et al. | |
| 8,401,659 B2 | 3/2013 | Von Arx et al. | |
| 8,706,251 B2 | 4/2014 | Von Arx et al. | |
| 10,272,251 B2 | 4/2019 | Kothandaraman et al. | |
| 2006/0099911 A1 | 5/2006 | Shibuya | |
| 2011/0022411 A1 | 1/2011 | Hjelm et al. | |
| 2011/0029043 A1* | 2/2011 | Frysz | A61N 1/37254 |
| | | | 607/116 |
| 2014/0061304 A1* | 3/2014 | Drees | G06Q 10/087 |
| | | | 235/385 |
| 2016/0042202 A1* | 2/2016 | Murray | A45C 13/10 |
| | | | 320/108 |
| 2021/0106834 A1 | 4/2021 | Kothandaraman et al. | |

* cited by examiner

1

SYSTEMS AND METHODS FOR
ESTABLISHING SECURE
COMMUNICATIONS BETWEEN MEDICAL
DEVICE SYSTEM COMPONENTS

This application claims the benefit of U.S. Provisional Application No. 63/346,460, filed May 27, 2022, the content of which is herein incorporated by reference in its entirety.

FIELD

Embodiments herein relate to medical device systems including features to enable secure wireless communications between components thereof.

BACKGROUND

Implantable medical devices are commonly used for many purposes including cardiac rhythm management, neuromodulation, drug delivery, monitoring, and the like.

Many implantable medical devices include components to facilitate wireless communications. Such wireless communications may include data regarding the patient and/or programming instructions for the implantable medical device. As such, there is a need for wireless communications with implantable devices to be secure.

SUMMARY

Embodiments herein relate to medical device systems including features to enable secure wireless communications between components thereof. In a first aspect, a medical device system is included having an implantable medical device and an implantable medical device packaging unit. The implantable device can include a control circuit and a communications antenna, wherein the communications antenna can be in electrical communication with the control circuit. The implantable device can be configured to fit within the implantable medical device packaging unit prior to implantation in a patient. A data bearing tag can also be included, wherein the data bearing tag can be disposed on or in the implantable medical device packaging unit. The system can also include an external communication device, wherein the external communication device can be configured to receive data from the data bearing tag enabling secure wireless communications between the implantable device and the external communication device.

In a second aspect, in addition to one or more of the preceding or following aspects, or in the alternative to some aspects, the data bearing tag can include at least one selected from the group consisting of an NFC tag, an optically recognizable code, and an RFID tag.

In a third aspect, in addition to one or more of the preceding or following aspects, or in the alternative to some aspects, the optically recognizable code can include a QR code.

In a fourth aspect, in addition to one or more of the preceding or following aspects, or in the alternative to some aspects, the NFC tag can include a passive NFC tag.

In a fifth aspect, in addition to one or more of the preceding or following aspects, or in the alternative to some aspects, the data bearing tag can include data in the form of a character string.

In a sixth aspect, in addition to one or more of the preceding or following aspects, or in the alternative to some aspects, the data bearing tag can include data in the form of at least one of a cryptography key and a digital certificate.

In a seventh aspect, in addition to one or more of the preceding or following aspects, or in the alternative to some aspects, the implantable medical device packaging unit can include electromagnetic shielding.

In an eighth aspect, in addition to one or more of the preceding or following aspects, or in the alternative to some aspects, the implantable device can include at least one selected from the group consisting of an implantable monitor, a cardiac rhythm management device, and a neuromodulation device.

In a ninth aspect, in addition to one or more of the preceding or following aspects, or in the alternative to some aspects, the external communication device can include a smart phone.

In a tenth aspect, in addition to one or more of the preceding or following aspects, or in the alternative to some aspects, the external communication device can include a personal patient communicator.

In an eleventh aspect, a medical device system can be included having an implantable device including a control circuit and a communications antenna. A data bearing tag can also be included, wherein the data bearing tag can be disposed on or in the implantable device. An external communication device can also be included, wherein the external communication device can be configured to receive data from the data bearing tag enabling secure wireless communications between the implantable device and the external communication device.

In a twelfth aspect, in addition to one or more of the preceding or following aspects, or in the alternative to some aspects, the data bearing tag can include at least one selected from the group consisting of an NFC tag, an optically recognizable code, and an RFID tag.

In a thirteenth aspect, in addition to one or more of the preceding or following aspects, or in the alternative to some aspects, the optically recognizable code can include a QR code.

In a fourteenth aspect, in addition to one or more of the preceding or following aspects, or in the alternative to some aspects, the NFC tag can include a passive NFC tag.

In a fifteenth aspect, in addition to one or more of the preceding or following aspects, or in the alternative to some aspects, the data bearing tag can include data in the form of a character string.

In a sixteenth aspect, in addition to one or more of the preceding or following aspects, or in the alternative to some aspects, the data bearing tag can include data in the form of at least one of a cryptography key and a digital certificate.

In a seventeenth aspect, in addition to one or more of the preceding or following aspects, or in the alternative to some aspects, the implantable device can include at least one selected from the group consisting of an implantable monitor, a cardiac rhythm management device, and a neuromodulation device.

In an eighteenth aspect, in addition to one or more of the preceding or following aspects, or in the alternative to some aspects, the external communication device can include a smart phone.

In a nineteenth aspect, in addition to one or more of the preceding or following aspects, or in the alternative to some aspects, the external communication device can include a personal patient communicator.

In a twentieth aspect, in addition to one or more of the preceding or following aspects, or in the alternative to some aspects, the implantable device can include a header structure, wherein the data bearing tag can be disposed on or within the header structure.

In a twenty-first aspect, in addition to one or more of the preceding or following aspects, or in the alternative to some aspects, the implantable device can include a housing, wherein the data bearing tag can be disposed on or within the housing.

In a twenty-second aspect, a method of providing secure wireless communications in a medical device system can be included, the method including providing a data bearing tag with an implantable medical device and exchanging data between the data bearing tag and an external communication device to enable secure wireless communications between the implantable medical device and the external communication device.

In a twenty-third aspect, in addition to one or more of the preceding or following aspects, or in the alternative to some aspects, the data bearing tag can include at least one selected from the group consisting of an NFC tag, an optically recognizable code, and an RFID tag.

In a twenty-fourth aspect, in addition to one or more of the preceding or following aspects, or in the alternative to some aspects, the optically recognizable code can include a QR code.

In a twenty-fifth aspect, in addition to one or more of the preceding or following aspects, or in the alternative to some aspects, the NFC tag can include a passive NFC tag.

In a twenty-sixth aspect, in addition to one or more of the preceding or following aspects, or in the alternative to some aspects, the data bearing tag can include data in the form of a character string.

In a twenty-seventh aspect, in addition to one or more of the preceding or following aspects, or in the alternative to some aspects, the data bearing tag can include data in the form of at least one of a cryptography key and a digital certificate.

In a twenty-eighth aspect, in addition to one or more of the preceding or following aspects, or in the alternative to some aspects, the method can further include enabling communication with the data bearing tag by removing the implantable medical device from a packaging unit prior to implantation.

In a twenty-ninth aspect, in addition to one or more of the preceding or following aspects, or in the alternative to some aspects, the packaging unit can include electromagnetic shielding, the electromagnetic shielding prevents communication with the data bearing tag.

In a thirtieth aspect, in addition to one or more of the preceding or following aspects, or in the alternative to some aspects, the implantable medical device can include at least one selected from the group consisting of an implantable monitor, a cardiac rhythm management device, and a neuromodulation device.

In a thirty-first aspect, in addition to one or more of the preceding or following aspects, or in the alternative to some aspects, the external communication device can include a smart phone.

In a thirty-second aspect, in addition to one or more of the preceding or following aspects, or in the alternative to some aspects, the external communication device can include a personal patient communicator.

In a thirty-third aspect, in addition to one or more of the preceding or following aspects, or in the alternative to some aspects, the data bearing tag can be disposed in or on the implantable medical device.

In a thirty-fourth aspect, a medical device system can be included having an implantable device including a control circuit and a communications antenna, wherein the communications antenna can be in electrical communication with the control circuit. The implantable device can also include an ultrasonic emitter, wherein the ultrasonic emitter can be in electrical communication with the control circuit. The system can also include an external communication device, wherein the external communication device can be configured to receive data transmitted ultrasonically from the ultrasonic emitter enabling secure wireless communications between the implantable device and the external communication device.

In a thirty-fifth aspect, in addition to one or more of the preceding or following aspects, or in the alternative to some aspects, the implantable device can include at least one selected from the group consisting of an implantable monitor, a cardiac rhythm management device, and a neuromodulation device.

In a thirty-sixth aspect, in addition to one or more of the preceding or following aspects, or in the alternative to some aspects, the external communication device can include a smart phone.

In a thirty-seventh aspect, a medical device system can be included having an implantable medical device packaging unit and an implantable device. The implantable device can include a control circuit and a communications antenna. The implantable device can be configured to fit within the implantable medical device packaging unit prior to implantation in a patient. A data bearing tag can also be included, wherein the data bearing tag can be disposed on or in the implantable medical device packaging unit. The medical device system can be configured to pass data from the data bearing tag to an external communication device thereby enabling secure wireless communications between the implantable device and the external communication device.

In a thirty-eighth aspect, in addition to one or more of the preceding or following aspects, or in the alternative to some aspects, the data bearing tag can include at least one selected from the group consisting of an NFC tag, an optically recognizable code, and an RFID tag.

In a thirty-ninth aspect, in addition to one or more of the preceding or following aspects, or in the alternative to some aspects, the optically recognizable code can include a QR code.

In a fortieth aspect, in addition to one or more of the preceding or following aspects, or in the alternative to some aspects, the NFC tag can include a passive NFC tag.

In a forty-first aspect, in addition to one or more of the preceding or following aspects, or in the alternative to some aspects, the data bearing tag can include data in the form of a character string.

In a forty-second aspect, in addition to one or more of the preceding or following aspects, or in the alternative to some aspects, the data bearing tag can include data in the form of at least one of a cryptography key and a digital certificate.

In a forty-third aspect, in addition to one or more of the preceding or following aspects, or in the alternative to some aspects, the implantable medical device packaging unit can include electromagnetic shielding.

In a forty-fourth aspect, in addition to one or more of the preceding or following aspects, or in the alternative to some aspects, the implantable device can include at least one selected from the group consisting of an implantable monitor, a cardiac rhythm management device, and a neuromodulation device.

In a forty-fifth aspect, a medical device system can be included having an implantable device including a control circuit and a communications antenna. A data bearing tag can be disposed on or in the implantable device. The medical device system can be configured to pass data from the data bearing tag to an external communication device thereby enabling secure wireless communications between the implantable device and the external communication device.

In a forty-sixth aspect, in addition to one or more of the preceding or following aspects, or in the alternative to some aspects, the data bearing tag can include at least one selected from the group consisting of an NFC tag, an optically recognizable code, and an RFID tag.

In a forty-seventh aspect, in addition to one or more of the preceding or following aspects, or in the alternative to some aspects, the optically recognizable code can include a QR code.

In a forty-eighth aspect, in addition to one or more of the preceding or following aspects, or in the alternative to some aspects, the NFC tag can include a passive NFC tag.

In a forty-ninth aspect, in addition to one or more of the preceding or following aspects, or in the alternative to some aspects, the data bearing tag can include data in the form of a character string.

In a fiftieth aspect, in addition to one or more of the preceding or following aspects, or in the alternative to some aspects, the data bearing tag can include data in the form of at least one of a cryptography key and a digital certificate.

In a fifty-first aspect, in addition to one or more of the preceding or following aspects, or in the alternative to some aspects, the implantable device can include at least one selected from the group consisting of an implantable monitor, a cardiac rhythm management device, and a neuromodulation device.

In a fifty-second aspect, in addition to one or more of the preceding or following aspects, or in the alternative to some aspects, the implantable device can include a header structure, wherein the data bearing tag can be disposed on or within the header structure.

In a fifty-third aspect, in addition to one or more of the preceding or following aspects, or in the alternative to some aspects, the implantable device can include a housing, wherein the data bearing tag can be disposed on or within the housing.

This summary is an overview of some of the teachings of the present application and is not intended to be an exclusive or exhaustive treatment of the present subject matter. Further details are found in the detailed description and appended claims. Other aspects will be apparent to persons skilled in the art upon reading and understanding the following detailed description and viewing the drawings that form a part thereof, each of which is not to be taken in a limiting sense. The scope herein is defined by the appended claims and their legal equivalents.

BRIEF DESCRIPTION OF THE FIGURES

Aspects may be more completely understood in connection with the following figures (FIGS.), in which.

Figure 1:
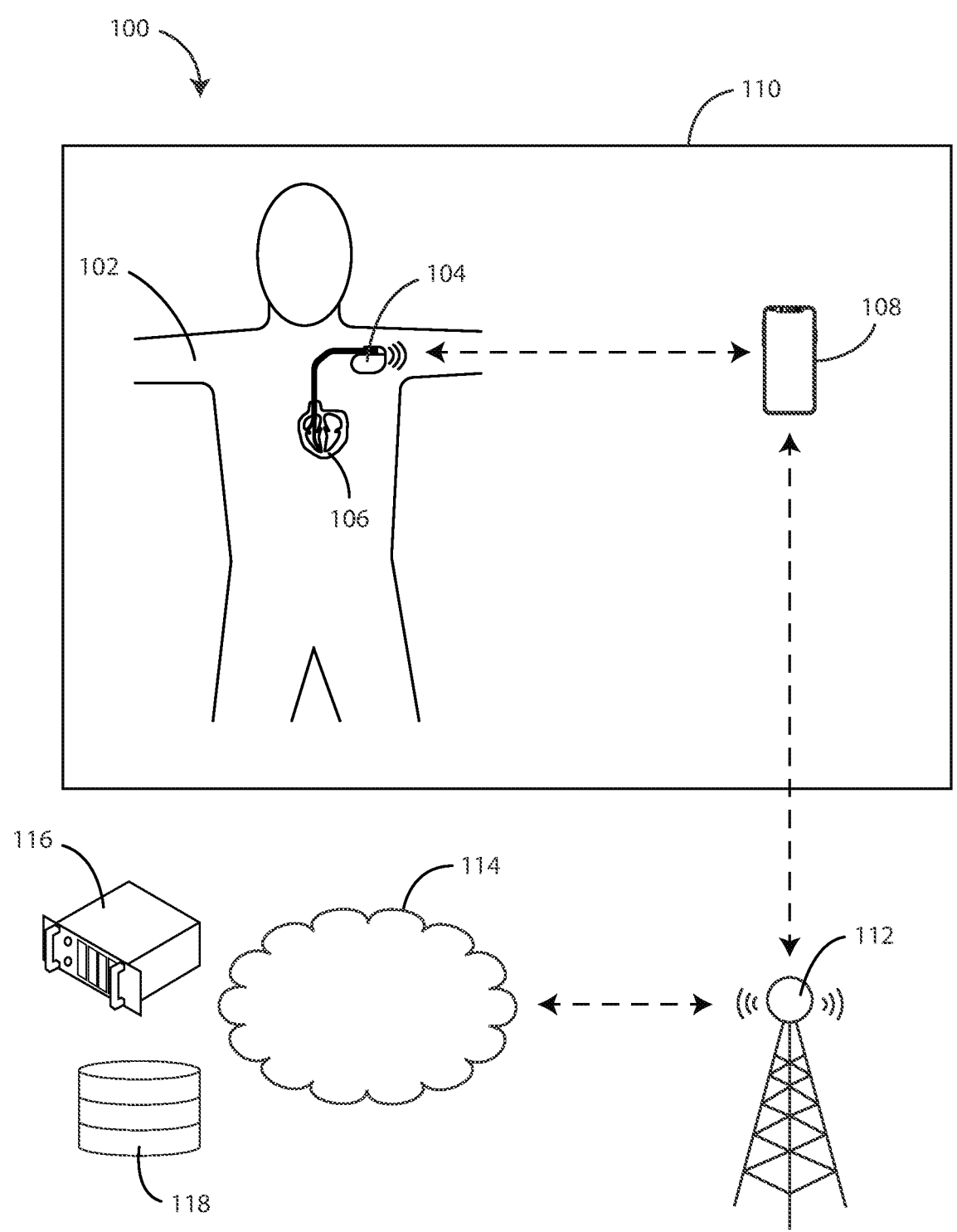
FIG. 1 is a schematic view of components of a medical device system in accordance with various embodiments herein.

While embodiments are susceptible to various modifications and alternative forms, specifics thereof have been shown by way of example and drawings, and will be described in detail. It should be understood, however, that the scope herein is not limited to the particular aspects described. On the contrary, the intention is to cover modifications, equivalents, and alternatives falling within the spirit and scope herein.

DETAILED DESCRIPTION

Wireless communications with implantable devices should be secure. One way to establish secure communication is to communicate a key, password, or token using a different communication technique or channel than used for ongoing secure communications. Security can be further enhanced if the key or password is transmitted at a time when it is unlikely that it could be intercepted or at a range sufficiently close it is unlikely that it could be intercepted.

Embodiments herein can include medical device systems wherein secure communications can be established by first passing security data such as a key, password, or token through a first communications channel then using the security data to support secure communications through a second channel. In various embodiments, the first communications channel is one that only works at short range to reduce or eliminate the chances that it could be intercepted. As an example, embodiments herein include a medical device system including an implantable device and an implantable medical device packaging unit. The implantable device can be configured to fit within the implantable medical device packaging unit prior to implantation in a patient, such as during storage or shipping after manufacturing and before implant. The implantable device can include a control circuit and a communications antenna in electrical communication with the control circuit.

The system can include a data bearing tag that includes the data necessary to establish secure communications through the second channel. Exemplary data bearing tags can include, but are not limited to, an NFC tag, an optically recognizable code, an RFID tag, or the like. The system can also include an external communication device. The external communication device can be configured to receive data from the data bearing tag enabling secure wireless communications between the implantable device and the external communication device.

Implanted medical devices are generally kept in a sterile state prior to implant in a patient. Maintaining their sterility during shipping and storage prior to implantation is facilitated by putting the medical device into a packaging unit that is hermetically sealed. In some embodiments, the data bearing tag can be disposed on or in the implantable medical device packaging unit. In this way, the data bearing tag can be secured prior to opening the packaging unit as part of the implant procedure for the implantable medical device.

However, in some cases, a data bearing tag enabling secure wireless communications can be disposed on or in the implantable device as opposed to with the packaging. As such, in some embodiments a medical device system is included having an implantable device with a control circuit and a communications antenna. The medical device system can also include a data bearing tag, wherein the data bearing tag is disposed on or in the implantable device. The system can also include an external communication device, wherein the external communication device is configured to receive data from the data bearing tag enabling secure wireless communications between the implantable device and the external communication device.

Referring now to FIG. 1, a schematic view of components of a medical device system 100 is shown in accordance with various embodiments herein. The medical device system 100 includes an implantable device 104. In various embodiments, the implantable device 104 at least one selected from the group consisting of an implantable monitor, a cardiac rhythm management device, and a neuromodulation device at least one selected from the group consisting of an implantable monitor, a cardiac rhythm management device, and a neuromodulation device.

The implantable device 104 can be implanted within a patient 102 to interface with their heart 106 or another organ. In this example, the medical device system 100 also includes an external communication device 108. The external communication device 108 can be, for example, a smart phone, a mobile computing device, a personal patient communicator, or another type of device for facilitating communication of data from the implantable device 104 to a data network. In various embodiments, the external communication device 108 can be configured to receive data from a data bearing tag enabling secure wireless communications between an implantable device 104 and an external communication device 108. Thus, the implantable device 104 can communicate wirelessly and securely with the external communication device 108. The patient 102, the implantable device 104, and the external communication device 108 can all be within the local environment 110. Communications may pass securely from the local environment 110 to a cell tower 112 as facilitated by the external communication device 108 and then onto the cloud 114 or another data network. In this example, the cloud 114 can include a server 116 (real or virtual) and a database 118 (real or virtual). However, the cloud 114 can also include other computing resources. While not shown in this view, a clinician can access information regarding the patient 102 as accessed through the cloud 114 or another data network.

In various embodiments herein, a data bearing tag herein used to establish secure communication between the medical device and an external communication device can be disposed on or in the packaging unit. In various embodiments, the data bearing tag can arranged so that it is inoperative until the packaging unit is opened. By way of example, in the context of an optical data bearing tag, the tag can be blocked from view until the packaging unit is opened. In the context of a data bearing tag that may communicate via wireless electromagnetic modalities (such as radio frequency-based communication or inductive based communication) the tag can be blocked from communication using electromagnetic shielding or the like. In this manner, the data bearing tag can only be utilized to facilitate secure communication between the medical device and an external communication device only when the packaging unit is opened.

Figure 2:
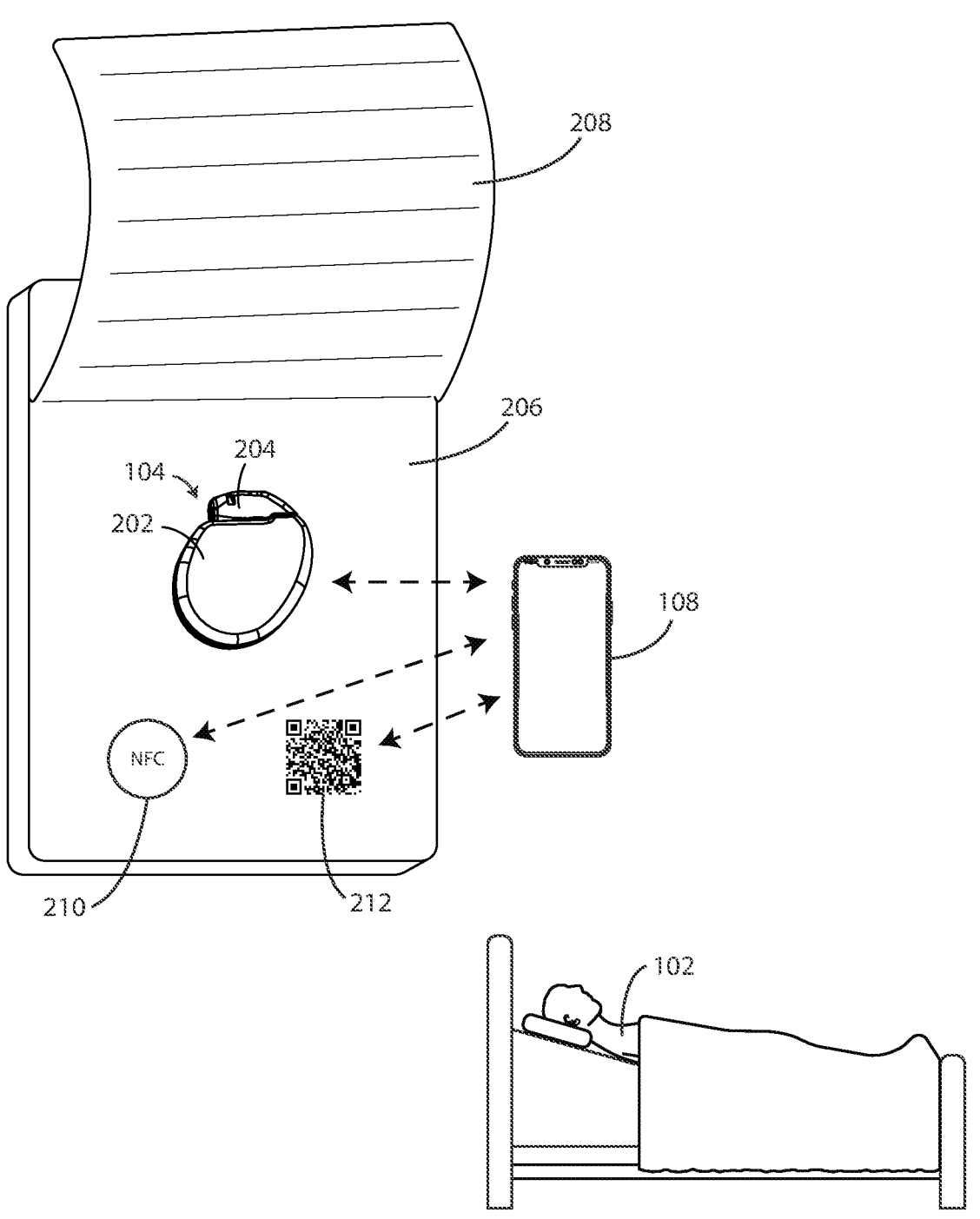
FIG. 2 is a schematic view of components of a medical device system in accordance with various embodiments herein.

Referring now to FIG. 2, a schematic view of components of a medical device system 100 is shown in accordance with various embodiments herein. The medical device system includes an implantable device 104 having a housing 202 and a header structure 204. The medical device system also includes an external communication device 108. The medical device system also includes an implantable medical device packaging unit 206. The implantable medical device packaging unit 206 includes a cover 208. A data bearing tag, such as a passive NFC tag 210 or a QR code 212 can be disposed on or in the packaging unit 206. In various embodiments, the implantable medical device packaging unit 206 can include electromagnetic shielding (such as that formed with conductive or magnetic materials).

Many different types of data bearing tags are envisioned herein. In various embodiments, the data bearing tag can include at least one including at least one of an NFC tag, an optically recognizable code, and an RFID tag. In various embodiments, the optically recognizable code can specifically include a QR code. In various embodiments, the NFC tag can specifically include a passive NFC tag.

The implantable medical device packaging unit 206 can take on various forms. In some embodiments, the packaging unit 206 can be a clamshell type construction, a tray with a sealing lid or cover, a sealed case, or the like.

In various embodiments, the data bearing tag can include data in the form of a character string. In various embodiments, the data bearing tag can include data in the form of a password or a token. In various embodiments, the data bearing tag can include data in the form of at least one of a cryptography key (such as a key for use with a Public/Private key encryption architecture) or a digital certificate.

In some cases, the data carried by the data bearing tag can include data beyond that which is necessary to establish secure communications. For example, in some embodiments, the data can also include information regarding the medical device itself, like a medical device model, a serial number, and the like.

In some embodiments, the data bearing tag can be disposed on or in the medical device itself within the packaging unit. For example, the data bearing tag can be disposed on or in a device housing that is part of the implantable medical device (such as a "can" in the context of an implantable cardiac rhythm management device) or on or in a header structure that can be part of some implantable medical devices (such as devices that include headers to facilitate the connection of electrical stimulation leads). In some embodiments, header structures herein can be formed of a polymer, such as a translucent or semi-translucent polymer.

Figure 3:
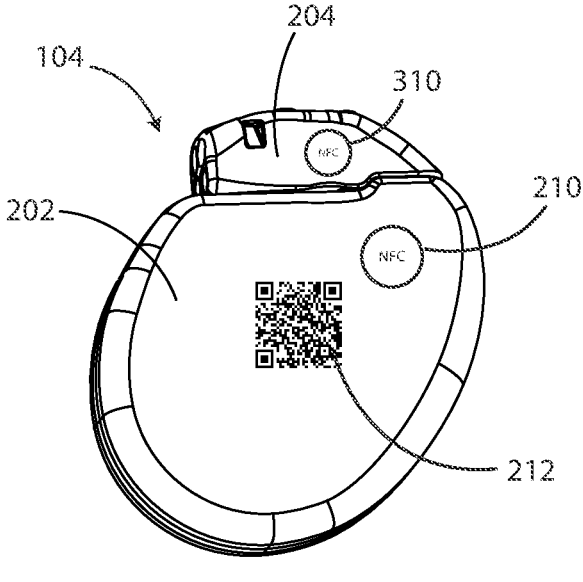
FIG. 3 is a schematic view of components of a medical device system in accordance with various embodiments herein.

Referring now to FIG. 3, a schematic view of components of a medical device system 100 is shown in accordance with various embodiments herein. As before, the medical device system includes an implantable device 104 and, in this example, the implantable device 104 includes a housing 202 and a header structure 204. A data bearing tag can be disposed on or in the housing 202 or the header structure 204. For example, a passive NFC tag 210 or a QR code 212 can be on the housing 202 as shown in FIG. 3. As another example, an NFC tag 310 can be disposed on or in the header structure 204. In some embodiments, the QR code 212 can be covered with a removable opaque sticker. In some embodiments, the NFC tag 210 can be covered with removable electromagnetic shielding. In some embodiments the housing 202 can be formed of a metal such as titanium, stainless steel, or the like. In some embodiments, the implanted medical device can include a ceramic window, such as a ceramic window on the housing 202 (e.g., defining a portion of the housing) which may otherwise be metal, and an NFC tag or antenna thereof can be positioned such that communications can pass through the ceramic window.

In some cases, an NFC tag disposed within the header structure 204 can specifically be a passive NFC tag. While not intending to be bound by theory, a passive NFC tag can be ideal for placement on or within a header structure 204 because a wired power source is not required for a passive NFC tag. In some embodiments, an NFC tag disposed on or within the housing 202 can be an active NFC tag. While an active NFC tag requires a power source attached thereto, it can communicate over a longer range and, for example, can be used to "wake up" another communication component such as a BLUETOOTH LE radio. While not intending to be bound by theory, an active NFC tag can be conducive for placement on or within the housing 202 as the housing 202 may include a power source.

It will be appreciated that while FIG. 3 shows two separate NFC tags and a QR code 212 that this is only to show various options and that only one of these may actually be needed to provide the data in order to establish secure communications as described herein. However, in some embodiments, a first and second technique of providing data to establish secure communications can be used. In some cases, these can be redundant in that only one need convey its data in order to establish secure communications herein. In other case, both may be required in order to establish secure communications herein (e.g., the data carried by each is not redundant and both may be required to establish secure communications herein). Requiring data from both (in this example with one channel being NFC radiofrequency and the other being optical) can dramatically enhance security.

Figure 4:
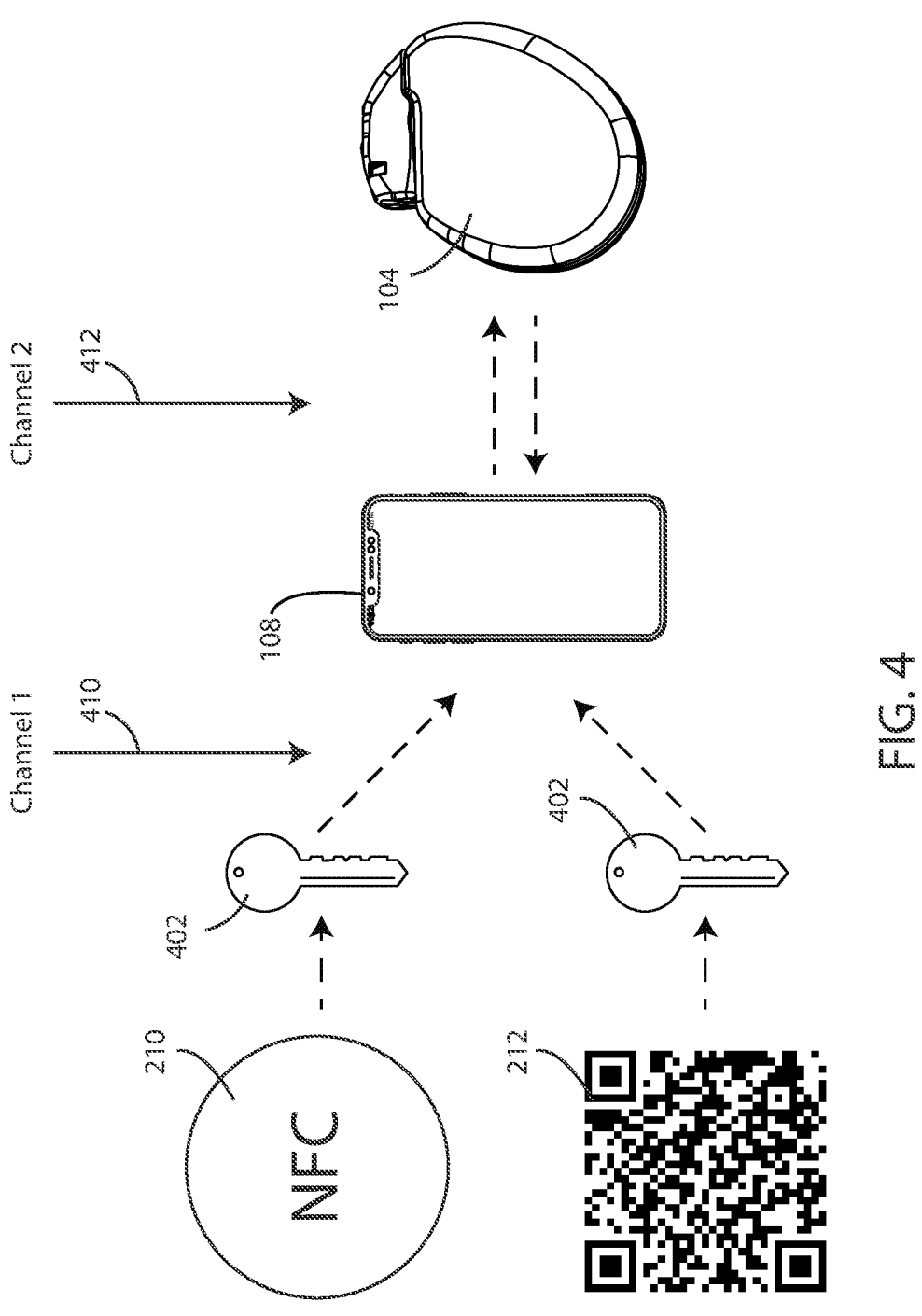
FIG. 4 is a schematic view of components of a medical device system in accordance with various embodiments herein.

The process of establishing secure communications can proceed in various ways. In many embodiments, the process can start by transmitting data needed for secure communications as carried by the data bearing tag to the device with which ongoing communications with the implantable device will be conducted (such as the external communication device 108). Referring now to FIG. 4, a schematic view of components of a medical device system 100 is shown in accordance with various embodiments herein. As before, the medical device system includes an implantable device 104 and an external communication device 108. A data bearing tag can be used as described herein such as in the form of a passive NFC tag 210 and/or a QR code 212.

In an initial communication phase, the data bearing tag can pass data to the external communication device, such as in the form of a key 402, using a first channel 410. The key 402 can then be used to establish secure wireless communication between the external communication device 108 and the implantable device 104 over a second channel 412. It will be appreciated that multiple types of external communication devices are contemplated herein. By way of example, in some embodiments the external communication device may be a smart phone or other mobile computing device. In some embodiments, the external communication device can be a personal patient communicator or a programmer device.

Figure 5:
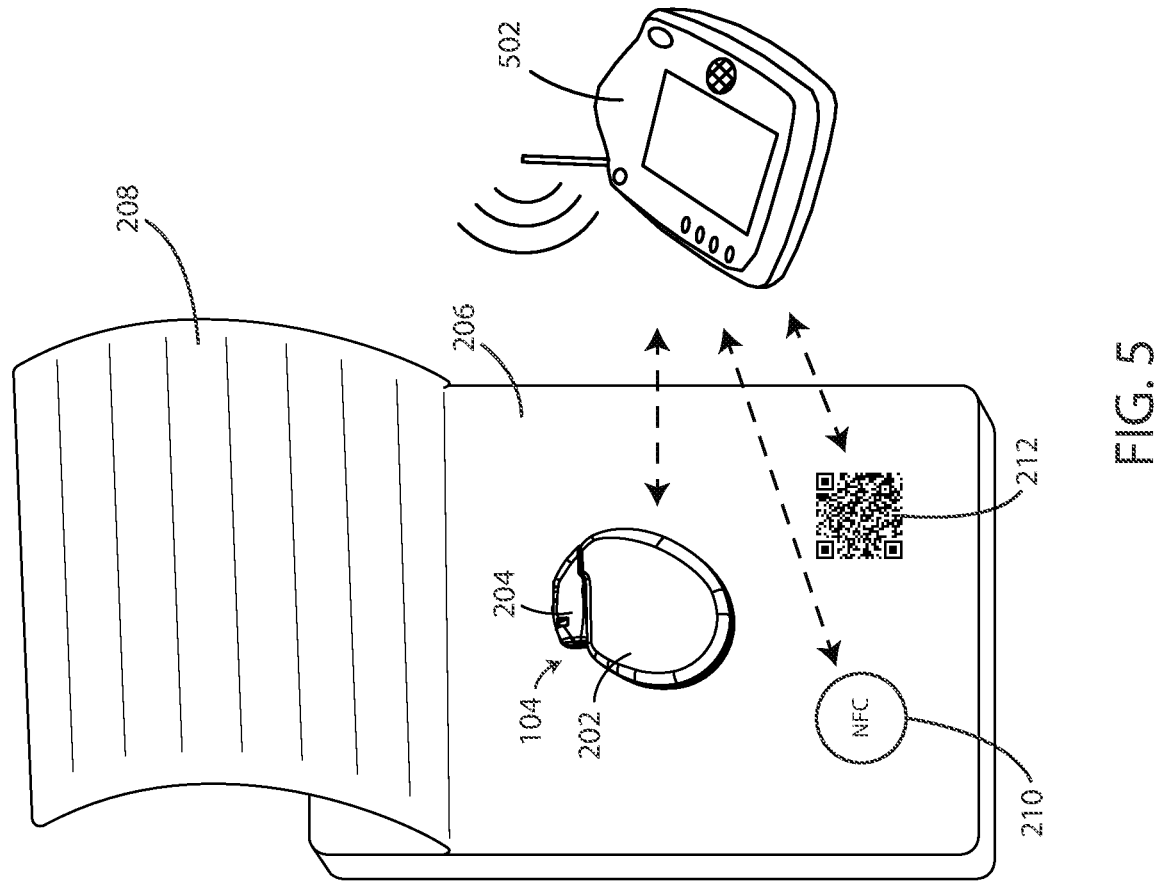
FIG. 5 is a schematic view of components of a medical device system in accordance with various embodiments herein.

Referring now to FIG. 5, a schematic view of components of a medical device system is shown in accordance with various embodiments herein. The medical device system includes an implantable device 104 with a housing 202 and a header structure 204. The medical device system also includes an implantable medical device packaging unit 206 with a cover 208. A data bearing tag is included such as a passive NFC tag 210 and/or a QR code 212. An external communication device is included and, in this example, includes a personal patient communicator 502.

It will be appreciated that multiple types of implantable medical devices are contemplated herein. By way of example, in some embodiments the implantable medical device can be an implantable monitoring device, such as an implantable cardiac monitor.

Figure 6:
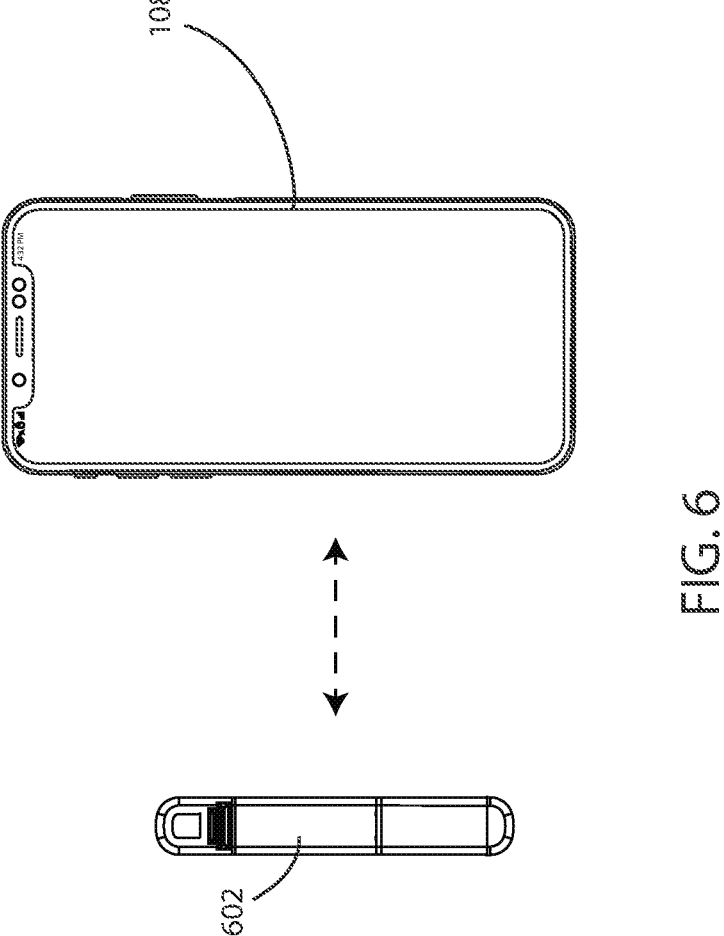
FIG. 6 is a schematic view of components of a medical device system in accordance with various embodiments herein.

Referring now to FIG. 6, a schematic view of components of a medical device system 100 is shown in accordance with various embodiments herein. The medical device system 100 includes an implantable monitor 602 and an external communication device 108.

In some embodiments, the techniques of establishing secure communication between two devices can also be used between other types of medical devices beyond just implantable medical devices. For example, techniques of establishing secure communication can be used to establish communication between a personal patient communicator and an external communication device.

Figure 7:
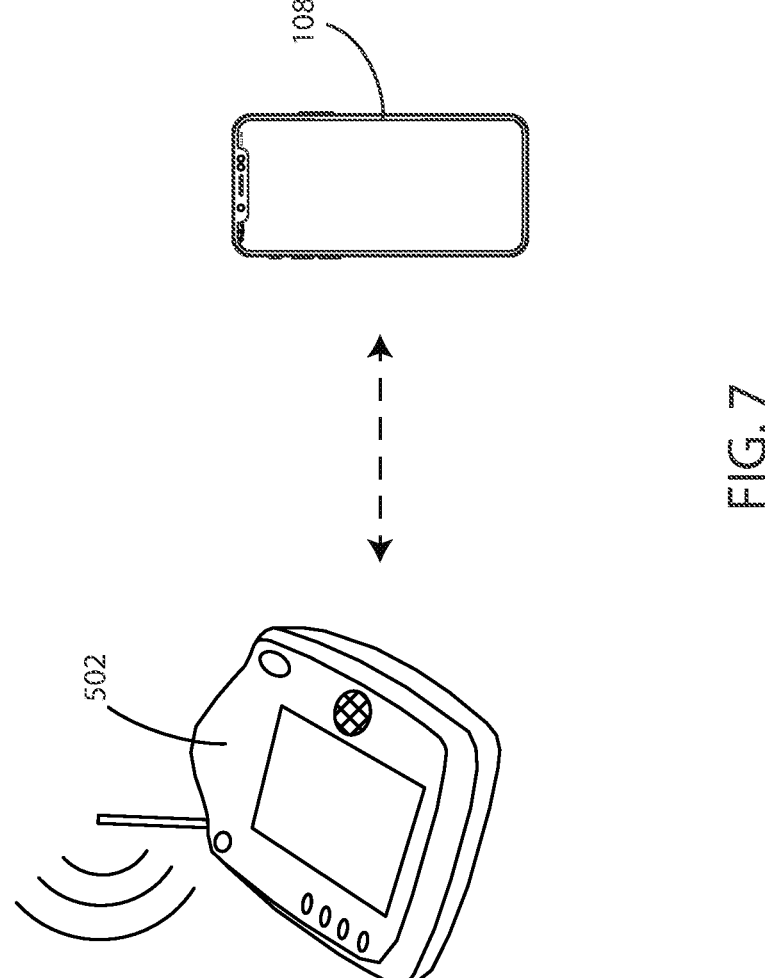
FIG. 7 is a schematic view of components of a medical device system in accordance with various embodiments herein.

Referring now to FIG. 7, a schematic view of components of a medical device system 100 is shown in accordance with various embodiments herein. In this example, the medical device system includes an external communication device 108 and a personal patient communicator 502.

Various different communication channels can be used to transfer data sufficient to setup secure communication between one device (such as an implantable medical device) and another device (such as an external communication device). In some embodiments it is a radiofrequency channel, an inductive based communication channel, or an optical channel. However, in some embodiments, data can be transferred to setup secure communication using ultrasonic communication as a channel. Ultrasonic communication channels can transmit and receive binary information by modulating signals with ultrasonic carrier waves.

For example, in various embodiments herein, a medical device system can include an implantable device with a control circuit. The implantable device can also include an ultrasonic component such as an emitter, receiver and/or transducer, wherein the ultrasonic component can be in electrical communication with the control circuit. The system can also include an external communication device. The external communication device can be configured to receive data transmitted ultrasonically from the ultrasonic emitter enabling secure wireless communications between the implantable device and the external communication device.

Figure 8:
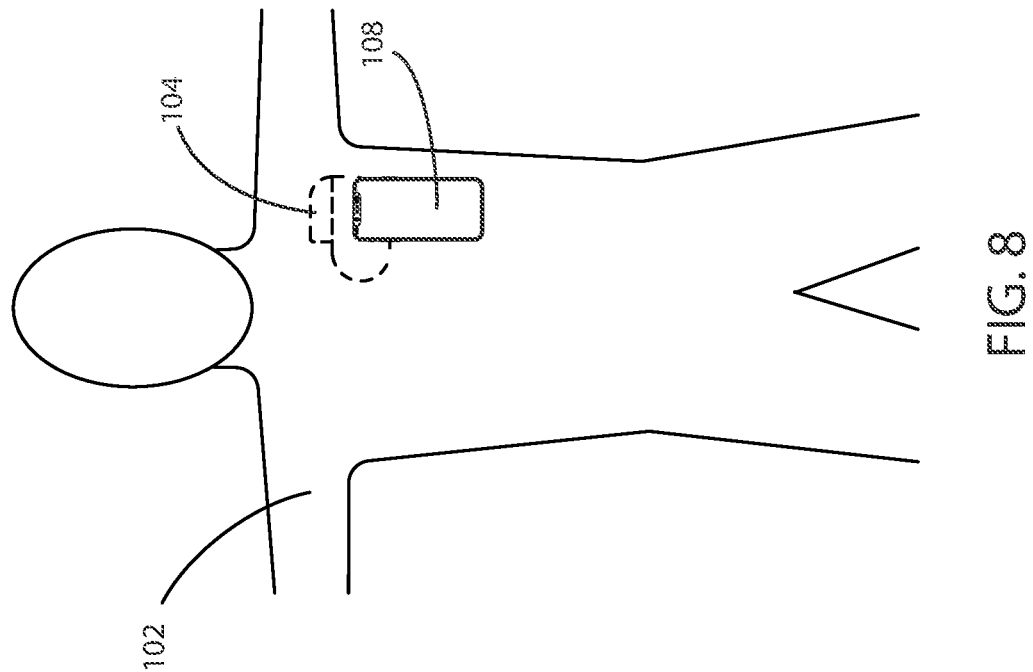
FIG. 8 is a schematic view of components of a medical device system in accordance with various embodiments herein.

Referring now to FIG. 8, a schematic view of components of a medical device system is shown in accordance with various embodiments herein. The medical device system includes an implantable device 104 implanted within a patient 102 and an external communication device 108 outside of the patient 102. In some embodiments, the external communication device 108 can be placed on or adjacent to the patient 102, such as on the patient's skin.

Placement in physical contact with the patient 102 can serve to enhance the ability to communicate through an ultrasonic channel. For example, placement in physical contact with the patient 102 can reduce ultrasonic transmission loss and/or increase the signal to noise ratio. As such, some embodiments herein can include an operation of contacting the patient with the external communication device with which secure communications are desired.

Beyond the aforementioned communication modalities that can be used as a channel to convey data needed to setup ongoing secure communications, other communication modalities that can be used herein can include acoustic communications and/or vibration-based communications. For example, a speaker (or other electroacoustic transducer) can be used to generate acoustic signals and/or vibrations and a microphone (of varying types) or an accelerometer can be used to pick up the signals. Both the implantable device as well as the external device can be configured to include components to allow for communication over an acoustic and/or vibration-based channel.

Figure 9:
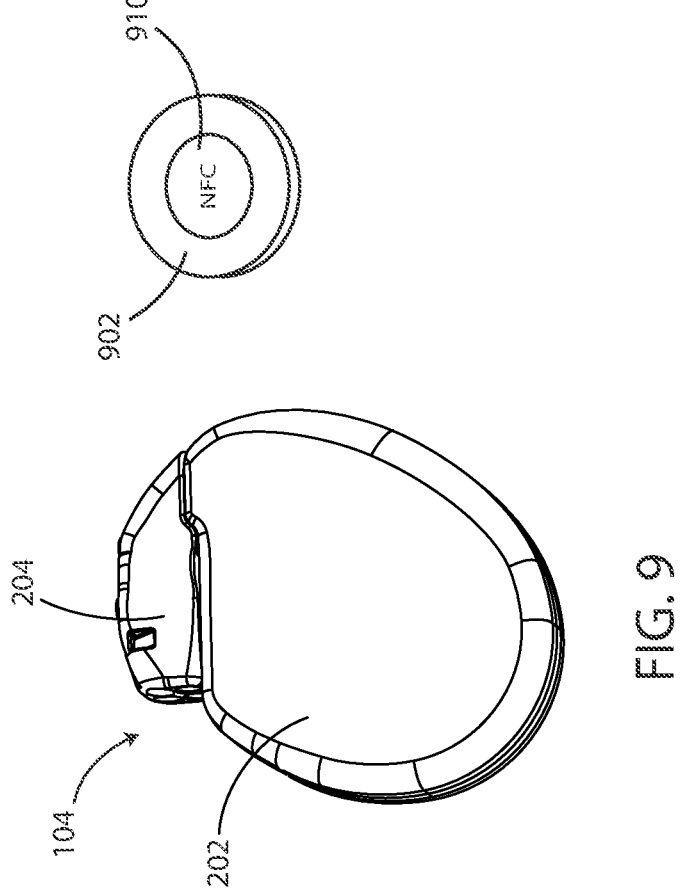
FIG. 9 is a schematic view of components of a medical device system in accordance with various embodiments herein.

In some embodiments, a separate component can be implanted along with the implantable medical device including a data bearing tag, such as an NFC tag. Referring now to FIG. 9, a schematic view is shown of components of a medical device system in accordance with various embodiments herein. As before, the medical device system includes an implantable device 104 having a housing 202 and a header structure 204. A data bearing tag in the form of an NFC tag 910 can be disposed on a carrier 902 or coupon. In practice, the carrier 902 can be provided during the implant procedure along with the implantable medical device 104 (for example, it can be disposed within the same packaging as the implantable medical device) and can be implanted subcutaneously, such as at the same time that the implantable medical device 104 is implanted. While not intending to be bound by theory, this approach can offer benefits in that the ability to communicate with the NFC tag 910 is compromised by potential interference with a metal housing 202 of the implantable device 104.

Figure 10:
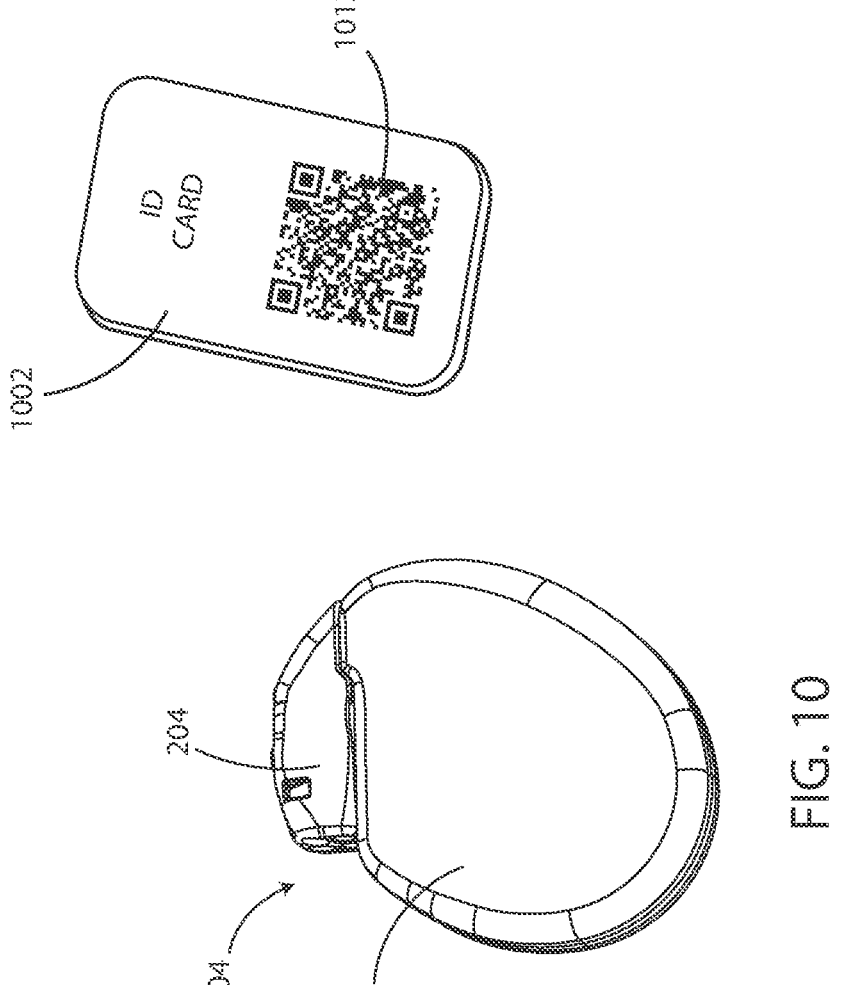
FIG. 10 is a schematic view of components of a medical device system in accordance with various embodiments herein.

In some embodiments, a data bearing tag can be provided entirely separately from the implanted medical device. For example, a data bearing tag can be disposed on a medical identification card and this card can be provided to the patient separately from the medical device itself. For example, the medical identification card can be mailed to (or otherwise provided to) the patient either before the procedure or after the procedure. Referring now to FIG. 10, a schematic view is shown of components of a medical device system in accordance with various embodiments herein. As before, the medical device system includes an implantable device 104 having a housing 202 and a header structure 204. A data bearing tag in the form of a QR code 1012 can be disposed on an identification card 1002. The identification card 1002 can be provided to the patient, such as mailed to the patient after the implant procedure. When it is desired to setup secured communications, a camera or other optical scanner on the external communication device 108 can be used to scan the QR code 1012 and the data encoded therein can correspond to data used herein to establish secure communications (e.g., a password, key, certificate, or other data, etc.). In some cases, if secure communication needs to be established with a new external communication device later on, then an identification card 1002 with a data bearing tag can be mailed to the patient.

Figure 11:
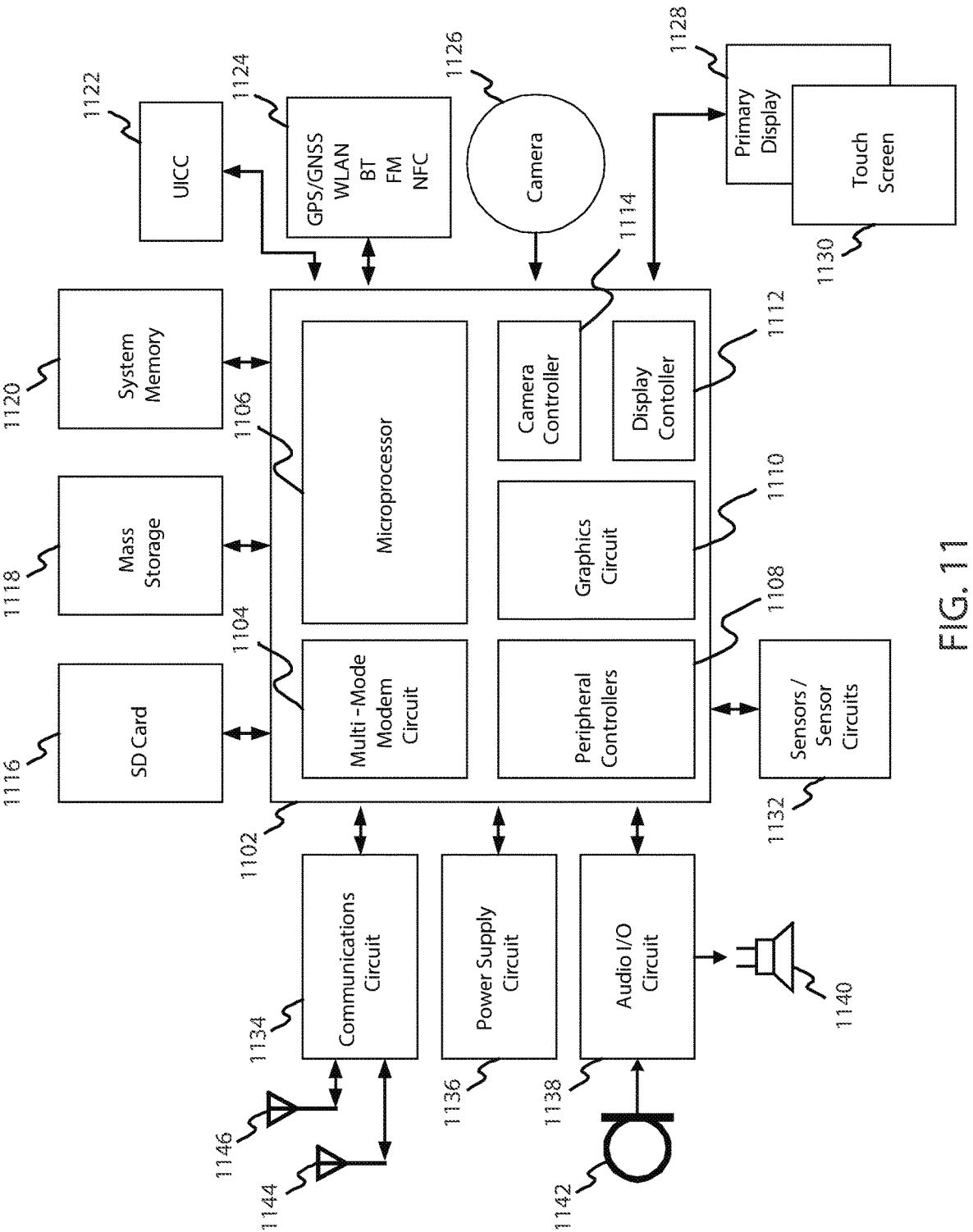
FIG. 11 is a block diagram of components of an external communication device in accordance with various embodiments herein.

External communication devices herein can include many different components. Referring now to FIG. 11, a block diagram is shown of components of an exemplary external communication device 108 in accordance with various embodiments herein. This block diagram is just provided by way of illustration and it will be appreciated that external communication device can include greater or lesser numbers of components. The external communication device in this example can include a control circuit 1102. The control circuit 1102 can include various components which may or may not be integrated. In various embodiments, the control circuit 1102 can include a microprocessor 1106, which could also be a microcontroller, FPGA, ASIC, or the like. The control circuit 1102 can also include a multi-mode modem circuit 1104 which can provide communications capability via various wired and wireless standards. The control circuit 1102 can include various peripheral controllers 1108. The control circuit 1102 can also include various sensors/sensor circuits 1132. The control circuit 1102 can also include a graphics circuit 1110, a camera controller 1114, and a display controller 1112. In various embodiments, the control circuit 1102 can interface with an SD card 1116, mass storage 1118, and system memory 1120. In various embodiments, the control circuit 1102 can interface with universal integrated circuit card (UICC) 1122. A spatial location determining circuit (or geolocation circuit) can be included and can take the form of an integrated circuit 1124 that can include components for receiving signals from GPS, GLO-NASS, BeiDou, Galileo, SBAS, WLAN, BT, FM, NFC type protocols, 5G picocells, or E911. In various embodiments, the external communication device can include a camera 1126. In various embodiments, the control circuit 1102 can interface with a primary display 1128 that can also include a touch screen 1130. In various embodiments, an audio I/O circuit 1138 can interface with the control circuit 1102 as well as a microphone 1142, a speaker 1140, and/or an ultrasonic receiver, emitter, or transducer. In various embodiments, a power supply or power supply circuit 1136 can interface with the control circuit 1102 and/or various other circuits herein in order to provide power to the system. In various embodiments, a communications circuit 1134 can be in communication with the control circuit 1102 as well as one or more antennas (1144, 1146). In some embodiments, the first antenna 1144 can be for communication through a first channel herein to provide data needed to setup secure communications. In some embodiments, the second antenna 1146 can be for ongoing secure communications through a second channel.

Figure 12:
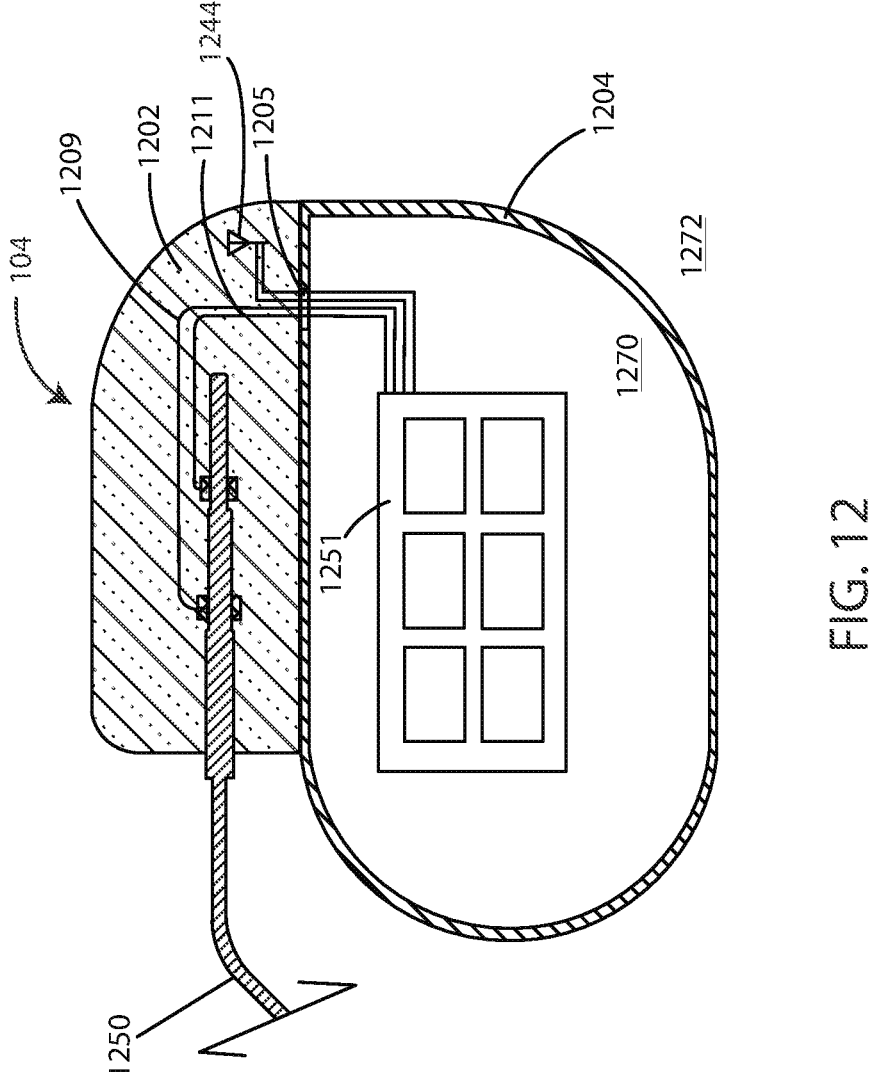
FIG. 12 is a schematic diagram of components of an implantable medical device in accordance with various embodiments herein.

Referring now to FIG. 12, a schematic diagram of components of an implantable medical device is shown in accordance with various embodiments herein. In this example, the implantable medical device 104 includes a header assembly 1202 and a housing 1204. The housing 1204 of the implantable medical device 104 can include various materials such as metals, polymers, ceramics, and the like. In one embodiment, the housing 1204 is formed of titanium. The header assembly 1202 can be coupled to one or more electrical stimulation leads 1250. The header assembly 1202 serves to provide fixation of the proximal end of one or more leads and electrically couples the leads to components within the housing 1204. The header assembly 1202 can be formed of various materials including metals, polymers, ceramics, and the like.

The housing 1204 defines an interior volume 1270 that is hermetically sealed off from the volume 1272 outside of the implantable device 104. Various electrical conductors 1209, 1211 can pass from the header assembly 1202 through a feed-through structure 1205, and into the interior volume 1270. As such, the conductors 1209, 1211 can serve to provide electrical communication between the electrical stimulation lead 1250 and circuitry 1251 disposed within the interior volume 1270 of the housing 1204. The circuitry 1251 can include various components such as a microprocessor or control circuit, memory (such as random access memory (RAM) and/or read only memory (ROM)), a telemetry module (which can include a telemetry antenna), electrical field sensor and stimulation circuitry, a power supply (such as a battery), and an optical sensor interface channel, amongst others.

The implantable medical device 104 can also include an antenna 1244 that can be disposed within the housing 1204 or, as shown in FIG. 12, within the header assembly 1202. In various embodiments, this antenna can used as part of a first channel to facilitate short range wireless communications, such as can be used herein to pass data which is then used to establish secure ongoing wireless communications through a second channel, such as with the telemetry module described previously.

Figure 13:
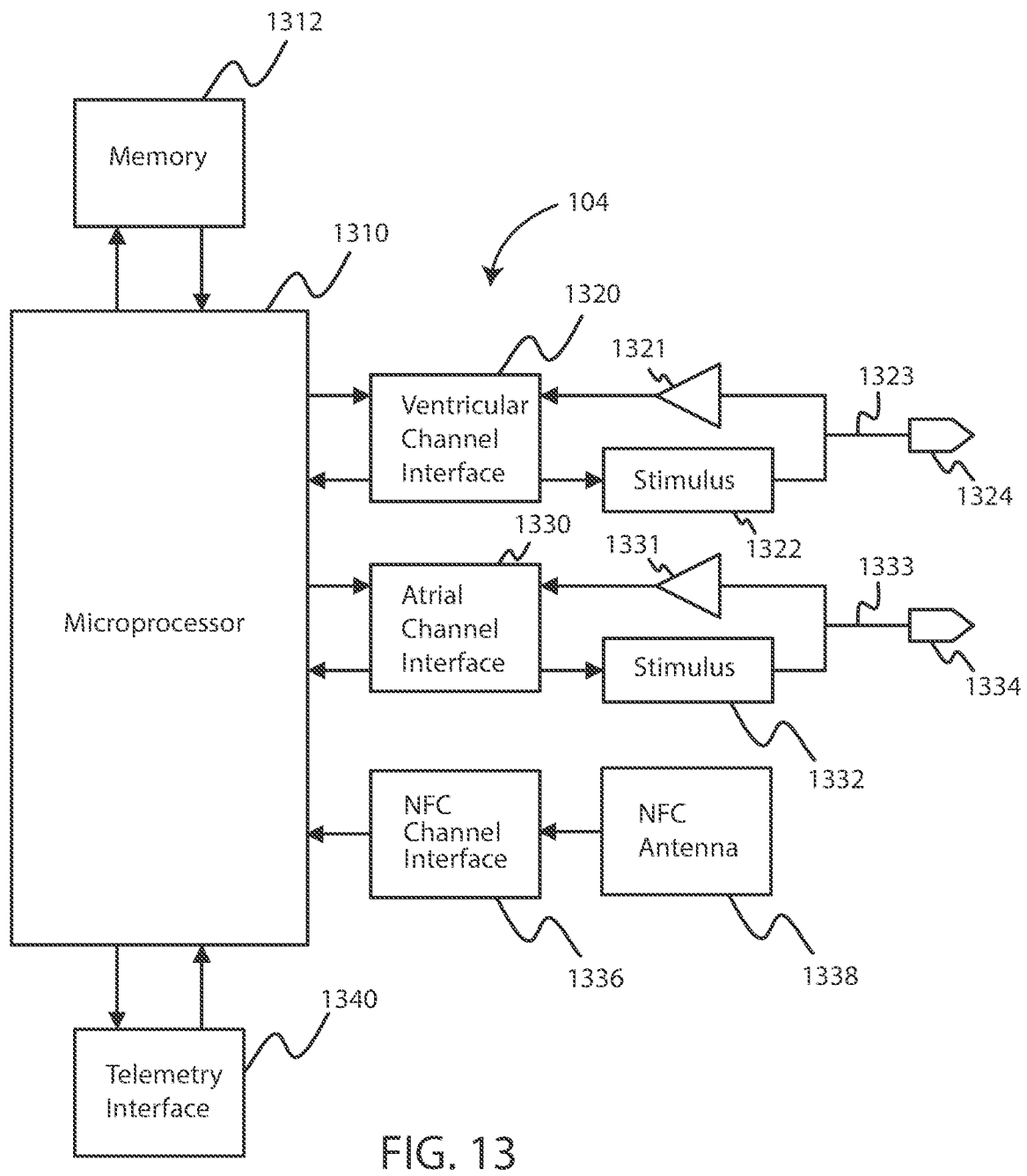
FIG. 13 is a block diagram of components of an implantable medical device in accordance with various embodiments herein.

Referring now to FIG. 13, a block diagram of components of an implantable medical device is shown in accordance with various embodiments herein. However, it will be appreciated that some embodiments can include additional elements beyond those shown in FIG. 13. In addition, some embodiments may lack some elements shown in FIG. 13. The implantable medical device of FIG. 13 is a cardiac rhythm management device, but other types of implantable medical devices are also included herein.

The implantable medical device 104 can sense cardiac events through one or more sensing channels and outputs pacing pulses to the heart via one or more pacing channels in accordance with a programmed pacing mode. A microprocessor 1310 can be part of a control circuit and can communicate with a memory 1312 via a bidirectional data bus. The memory 1312 typically comprises read only memory (ROM) or random access memory (RAM) for program storage and RAM for data storage.

The implantable medical device can include atrial sensing and pacing channels comprising at least a first electrode 1334, lead 1333, sensing amplifier 1331, output circuit 1332, and an atrial channel interface 1330 which can communicate bidirectionally with a port of microprocessor 1310. In this embodiment, the device also has ventricular sensing and pacing channels comprising at least a second electrode 1324, lead 1323, sensing amplifier 1321, output circuit 1322, and ventricular channel interface 1320. For each channel, the same lead and electrode are used for both sensing and pacing. The channel interfaces 1320 and 1330 include analog-to-digital converters for digitizing sensing signal inputs from the sensing amplifiers and registers which can be written to by the control circuitry in order to output pacing pulses, change the pacing pulse amplitude, and adjust the gain and threshold values for the sensing amplifiers.

The implantable medical device can also include an NFC antenna 1338 (or another type of wireless communication antenna) and an NFC channel interface 1336. A telemetry interface 1340 can be provided for communicating with an external device, such as an external communication device herein or another type of external device like a programmer. Thus, in this example the NFC antenna 1338 (part of a first channel) can be used for providing data used to setup secure communications between the implanted device and the external communication device which is then conducted over the telemetry interface (part of a second channel).

As described above, the data provided by the data bearing tag can facilitate secure communications between the implantable medical device and the external communication device or another external device. The data can be in the form of a password, a token, a key, a digital certificate, or other code or characters. Various shared key authentication techniques can be used including, but not limited to, wired equivalent privacy (WEP), WPA, WPA2, WPA3, or the like. Various pairing and/or handshake protocols can be used including 3-way handshakes, 4-way handshakes, or the like. For example, the protocol can include one or more of a probe request and response, an authentication request and response, and an association request and response. After establishing a secure connection, the ongoing wireless communications can include data that is encrypted by using methods such as temporal key integrity protocol (TKIP), advanced encryption standard (AES), Galois/Counter mode protocol (GCMP), or the like. In some embodiments, the communications can follow a secure BLUETOOTH protocol (or variants thereof like BLUETOOTH LOW ENERGY), a secure WIFI protocol, or another wireless protocol supporting secure communications. Wireless frequencies used for ongoing wireless communication can vary, but in some embodiments can include frequencies ranging from 3 kHz to 300 GHz, such as frequency bands including one or more of 900 MHz, 2.4 GHz, 3.6 GHz, 4.9 GHz, 5 GHz, 5.9 GHz, 6 GHz and 60 GHz. In various embodiments, an ISM band can be used at 2.4 to 2.485 GHZ.

In some embodiments, the security data (conveyed by the data bearing tag or otherwise) needed to establish secure communications can also be used for other purposes. For example, in some embodiments, the security data can be used to authorize/enable specific functionality on the part of the external communication device. In some embodiments, the security data can be used to unlock certain functionality of the external communication device (for example putting the implanted device into an MRI-safe operating mode). In some embodiments, the security data can be used to cause the implanted medical device to accept a predetermined set of programming commands (such as putting the implanted device into an MRI-safe operating mode) from the external communication device.

Methods

Many different methods are contemplated herein, including, but not limited to, methods of making, methods of using, and the like. Aspects of system/device operation described elsewhere herein can be performed as operations of one or more methods in accordance with various embodiments herein.

In various embodiments, operations described herein and method steps can be performed as part of a computer-implemented method executed by one or more processors of one or more computing devices. In various embodiments, operations described herein and method steps can be implemented as instructions stored on a non-transitory, computer-readable medium that, when executed by one or more processors, cause a system to execute the operations and/or steps.

In an embodiment, a method of providing secure wireless communications in a medical device system is included, the method can include providing a data bearing tag with an implantable medical device and exchanging data between the data bearing tag and an external communication device to enable secure wireless communications between the implantable medical device and the external communication device.

In an embodiment, the data bearing tag can include at least one selected from the group consisting of an NFC tag, an optically recognizable code, and an RFID tag. In an embodiment, the optically recognizable code can include a QR code. In an embodiment, the NFC tag can include a passive NFC tag.

In an embodiment, the data bearing tag can include data in the form of a character string. In an embodiment, the data bearing tag can include data in the form of at least one of a cryptography key and a digital certificate.

In an embodiment, the method can further include enabling communication with the data bearing tag by removing the implantable medical device from a packaging unit prior to implantation. In an embodiment, the packaging unit can include electromagnetic shielding, wherein the electromagnetic shielding prevents communication with the data bearing tag.

It should be noted that, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

It should also be noted that, as used in this specification and the appended claims, the phrase "configured" describes a system, apparatus, or other structure that is constructed or configured to perform a particular task or adopt a particular configuration. The phrase "configured" can be used interchangeably with other similar phrases such as arranged and configured, constructed and arranged, constructed, manufactured and arranged, and the like.

All publications and patent applications in this specification are indicative of the level of ordinary skill in the art to which this invention pertains. All publications and patent applications are herein incorporated by reference to the same extent as if each individual publication or patent application was specifically and individually indicated by reference.

As used herein, the recitation of numerical ranges by endpoints shall include all numbers subsumed within that range (e.g., 2 to 8 includes 2.1, 2.8, 5.3, 7, etc.).

The headings used herein are provided for consistency with suggestions under 37 CFR 1.77 or otherwise to provide organizational cues. These headings shall not be viewed to limit or characterize the invention(s) set out in any claims that may issue from this disclosure. As an example, although the headings refer to a "Field," such claims should not be limited by the language chosen under this heading to describe the so-called technical field. Further, a description of a technology in the "Background" is not an admission that technology is prior art to any invention(s) in this disclosure. Neither is the "Summary" to be considered as a characterization of the invention(s) set forth in issued claims.

The embodiments described herein are not intended to be exhaustive or to limit the invention to the precise forms disclosed in the following detailed description. Rather, the embodiments are chosen and described so that others skilled in the art can appreciate and understand the principles and practices. As such, aspects have been described with reference to various specific and preferred embodiments and techniques. However, it should be understood that many variations and modifications may be made while remaining within the spirit and scope herein.

The invention claimed is:

1. A medical device system comprising:
an implantable medical device packaging unit; and
an implantable device, the implantable device comprising
    a control circuit; and
    a communications antenna, wherein the communications antenna is in electrical communication with the control circuit;

wherein the implantable device is configured to fit within the implantable medical device packaging unit prior to implantation in a patient;
a data bearing tag, wherein the data bearing tag is disposed on or in the implantable medical device packaging unit; and
an external communication device, wherein the external communication device is configured to receive data from the data bearing tag enabling secure wireless communications between the implantable device and the external communication device.

2. The medical device system of claim 1, the data bearing tag comprising at least one selected from the group consisting of an NFC tag, an optically recognizable code, and an RFID tag.

3. The medical device system of claim 2, the optically recognizable code comprising a QR code.

4. The medical device system of claim 2, the NFC tag comprising a passive NFC tag.

5. The medical device system of claim 1, the data bearing tag comprising data in the form of a character string.

6. The medical device system of claim 1, the data bearing tag comprising data in the form of at least one of a cryptography key and a digital certificate.

7. The medical device system of claim 1, the implantable medical device packaging unit comprising electromagnetic shielding.

8. The medical device system of claim 1, the implantable device comprising at least one selected from the group consisting of an implantable monitor, a cardiac rhythm management device, and a neuromodulation device.

9. The medical device system of claim 1, wherein the data bearing tag is configured to be inoperative until the implantable medical device packaging unit is opened.

10. The medical device system of claim 9, wherein the data bearing tag is configured to communicate via wireless electromagnetic modalities, and wherein electromagnetic shielding prevents wireless communication with the data bearing tag until the implantable medical device packaging unit is opened.

11. The medical device system of claim 1, further comprising a second data bearing tag, wherein the external communication device is configured to receive data from the data bearing tag and the second data bearing tag enabling secure wireless communications between the implantable device and the external communication device.

12. The medical device system of claim 11, the data bearing tag and the second data bearing tag each comprising different data required to establish secure communications, wherein the data bearing tag and the second data bearing tag must be read to enable secure communications.

13. A medical device system comprising:
an implantable device, the implantable device comprising
    a control circuit; and
    a communications antenna, wherein the communications antenna is in electrical communication with the control circuit;
a data bearing tag, wherein the data bearing tag is disposed on or in the implantable device; and
an external communication device, wherein the external communication device is configured to receive data from the data bearing tag enabling secure wireless communications between the implantable device and the external communication device.

14. The medical device system of claim 13, the data bearing tag comprising at least one selected from the group consisting of an NFC tag, an optically recognizable code, and an RFID tag.

15. The medical device system of claim 14, the optically recognizable code comprising a QR code.

16. The medical device system of claim 14, the NFC tag comprising a passive NFC tag.

17. The medical device system of claim 13, the data bearing tag comprising data in the form of a character string.

18. The medical device system of claim 13, the data bearing tag comprising data in the form of at least one of a cryptography key and a digital certificate.

19. The medical device system of claim 13, the implantable device comprising at least one selected from the group consisting of an implantable monitor, a cardiac rhythm management device, and a neuromodulation device.

20. The medical device system of claim 13, the implantable device comprising a header structure, wherein the data bearing tag is disposed on or within the header structure.

\* \* \* \* \*